US006106827A

United States Patent [19]
La Gamma et al.

[11] Patent Number: 6,106,827
[45] Date of Patent: *Aug. 22, 2000

[54] METHOD OF PRODUCING GENETICALLY MODIFIED ASTROCYTES AND USES THEREOF

[75] Inventors: Edmund F. La Gamma, Setauket; Gary Weisinger, Commack; Robert E. Strecker, Port Jefferson; Nicholas J. Lenn, East Setauket, all of N.Y.

[73] Assignee: The Research Foundation of State University of New York, Albany, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/862,438

[22] Filed: May 24, 1997

Related U.S. Application Data

[63] Continuation of application No. 07/909,281, Jul. 6, 1992, abandoned.
[51] Int. Cl.$^7$ .............. C12N 15/85; C12N 5/08; C12N 5/06; C12N 15/63
[52] U.S. Cl. ............ 424/93.21; 435/69.1; 435/70.1; 435/325; 435/363; 435/368; 435/455
[58] Field of Search ............ 424/93.21; 435/375, 435/320.1, 6, 69.1, 91.1, 172.1, 172.3, 325, 363, 368, 70.1, 455; 536/24.1, 24.5, 23.1, 23.2; 514/44

[56] References Cited

U.S. PATENT DOCUMENTS

| | | | |
|---|---|---|---|
| 5,082,670 | 1/1992 | Gage et al. | 424/520 |
| 5,190,931 | 3/1993 | Inouye | 435/91.32 |

FOREIGN PATENT DOCUMENTS

WO 90/06757   6/1990   WIPO.

OTHER PUBLICATIONS

Plautz et al. Selective elimination of recombinant genes in vivo with a suicide retroviral vector. New Biologist 3(7):709–715. Abstract only, Jul. 1991.
I. Maxwell et al. Cancer Research, vol. 46, (1986) pp. 4660–4664.
B. Morris (Complete Article) Neuroscience, vol. 25 (1988) pp. 525–532.
T. Friedmann Sci. Amer. Jun. '97, pp. 96–101.
I. Verma et al. Nature 389:239–42 '97.
S. Orkin et al.—NIH Assessment of Gene Therapy Dec. 7, 1995.
M. Melner et al. EMBO J. 9 (3) :791–6 ('90).
L. Mucke et al. The New Biologist ('91) 3(5): 465–74.
J. Sarid J. Neuro Sci. Res. 28 : 217–228 ('91).
R. McIvor et al. Mol. Cell Biol. ('85) 5(6): 1349–57.
N. Rosenthal Meth. Enzymol. 152 : 704–20 ('87).
E. Bonnelli et al. PNAS (Oct. 1988) 85: 7572–76.
Shinoda et al. Science, vol. 245 ('89) pp. 415–417.
Goetz et al. New Engl. J. of Med., vol. 320 ('89) pp. 337–341.
Gill et al. J. Amer. Med. Assoc., vol. 261 ('89) pp. 2674–2676.
Pollack et al. J. Neurosci. Res., vol. 31 (1992) pp. 33–45.
Cunningham et al. Brain Research, vol. 561 ('91) pp. 192–202.
Emmett et al. Brain Research, vol. 447 ('88) pp. 223–233.
Kimelberg et al. "Astrocytes", Scientific Amer., vol. 260 ('89) pp. 66–76.
Olson et al. Endocrinology, vol. 129 ('91) pp. 1066–1074.
Sarver et al. Annuals of N.Y. Acad. of Sci.
Moolten, Cancer Research, vol. 46 ('86) pp. 5276–5281.
Morris et al. (Abstract) Neuroscience, vol. 25 (#2) (1988) 525–532.
Choo et al. DNA, vol. 5, #6 ('86) pp. 529–537.
Comb et al. Nature, vol. 323 ('86) pp. 353–356.
Sambrook et al. "Molecular Cloning," Cold Spr. Harbor, NY, CSH Press, 1989, pp. 16.39–16.40, 16.54–16.55.
W.J. Freed et al, Progress in Brain Research 82: 11–20 (1990).
B. Alberts et al., "Molecular Biology of the Cell", Garland Publishing, Inc., New York, pp.1016–1018, 1079 (1983).
A. Bjorklund, TINS 14: 319–322 (1991).
W.F. Blakemore and R.J.M. Franklin, Trends in Neurosciences 14: 323–327 (1991).
E. Cattaneo and R. McKay, Trends in Neurosciences 14: 338–340 (1991).
L.J. Fisher et al., Neuron 6: 371–380 (1991).
D. Erickson, Scientific American, pp. 134, 136 (Jan. 1992).
T. Friedmann, Science 244: 1275–1281 (1989).
F.H. Gage and L.J. Fisher, Neuron 6: 1–12 (1991).
F.H. Gage et al., Neuroscience 23: 795–807 (1987).
F.H. Gage et al., Progress in Brain Research 82: 1–10 (1990).
F.H. Gage et al., Trends in Neurosciences 14: 328–335 (1991).
B.J. Hoffer and L. Olson, Trends in Neurosciences 14: 384–387 (1991).
M. Hoffman, Science 256: 445 (1992).
P. Horellou et al., Neuron 5: 393–402 (1990).
F. D. Ledley, International Pediatrics 7: 7–15 (1992).
O. Lindvall, Trends in Neurosciences 14: 376–382 (1991).

(List continued on next page.)

*Primary Examiner*—Karen M. Hauda
*Assistant Examiner*—Anne-Marie Baker
*Attorney, Agent, or Firm*—John P. White; Cooper & Dunham LLP

[57] ABSTRACT

A genetically modified astrocyte for gene therapy is provided. The genetically modified astrocyte includes one or more stably introduced DNA sequences selected from DNA encoding a selectable marker, DNA encoding a poison pill, and DNA encoding a molecule useful for gene therapy. The genetically modified astrocyte may be produced utilizing plasmids and non-viral transfection methods, as are also provided by the subject invention. Methods for producing and utilizing the genetically modified astrocytes and regulating the engineered products, as well as kits thereof, are further provided.

10 Claims, 14 Drawing Sheets

OTHER PUBLICATIONS

M. Miura et al., Journal of Neurochemistry 55: 1180–1188 (1990).

B. A. Reynolds and S. Weiss, Science 255: 1707–1710 (1992).

D.J. Sloan et al., Trends in Neurosciences 14: 341–346 (1991).

J.A. Wolff et al., Proc. Natl. Acad. Sci. USA 86: 9011–9014 (1989).

ASM News 58: 67–69 (Feb. 1992).

"Introduction of DNA into Mammalian Cells", in Current Protocols in Molecular Biology, Wiley & Sons, New York, New York Supp. 14, 9.0.1–9.9.3 (1991).

The Economist, pp. 95–97 (Apr. 25, 1992).

L. Thompson, Science 255: 1072 (1992).

N. Angier, New York Times, "New Nerve Tissue is Generated from the Brain Cells of Mice", pp. A1 and A18 (Mar. 27, 1992).

J.E. Bishop, The Wall Street Journal, "Nova Pharmaceutical Seeks Treatments for Diseases Using Test–Tube Brain Cells", p. B3 (Mar. 15, 1991).

M. Barinaga, Science 255: 1646 (1992).

A. Pollack, The New York Times, "Gene Therapy Gets the Go–Ahead", p. D1 and D5 (Feb. 14, 1992).

F.E. Bloom, in Psychopharmacology: The Third Generation of Progress, edited by H. Y. Meltzer, Raven Press, New York, Chap. 182, p. 1685, 1687 1688 (1987).

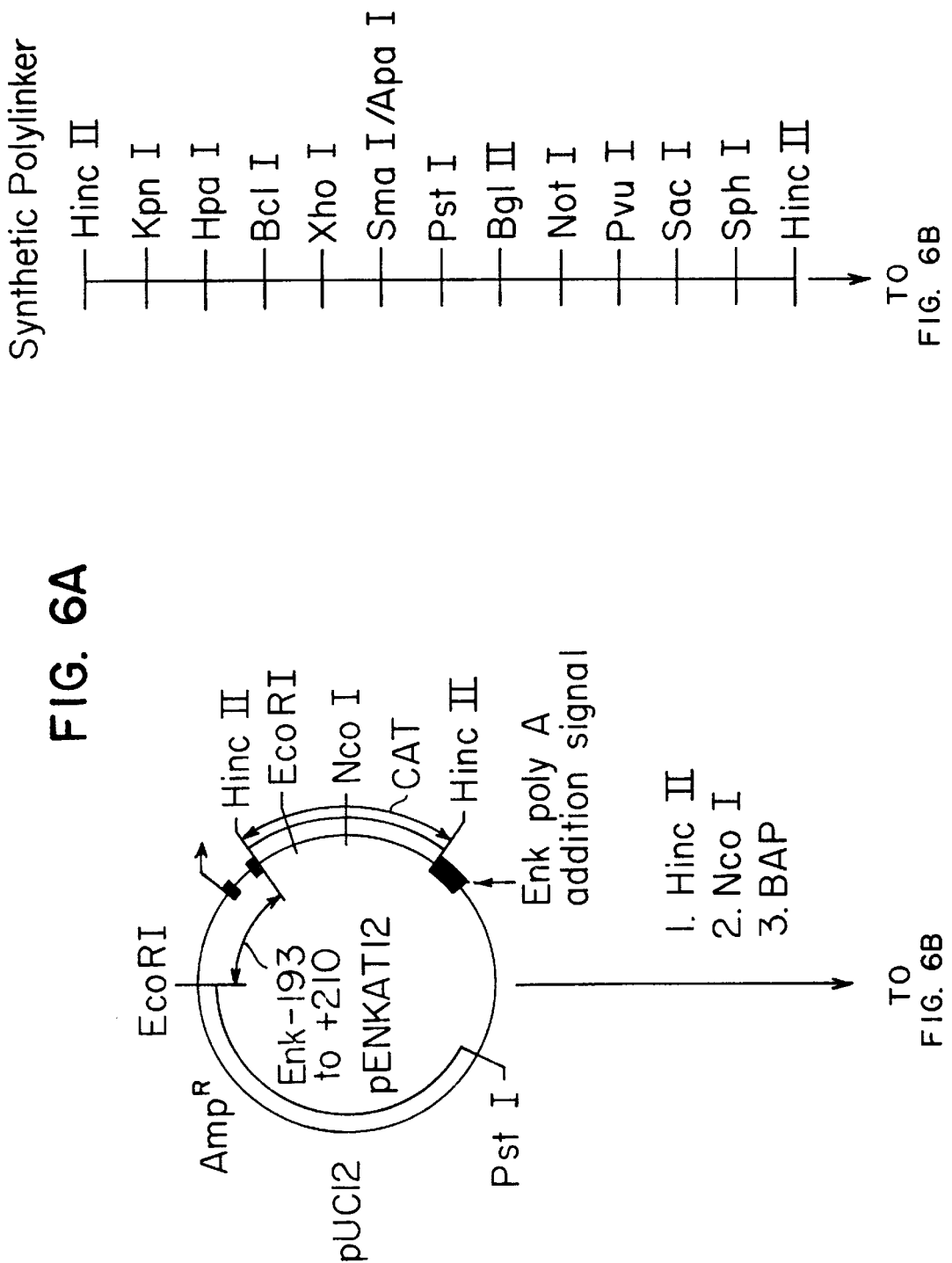

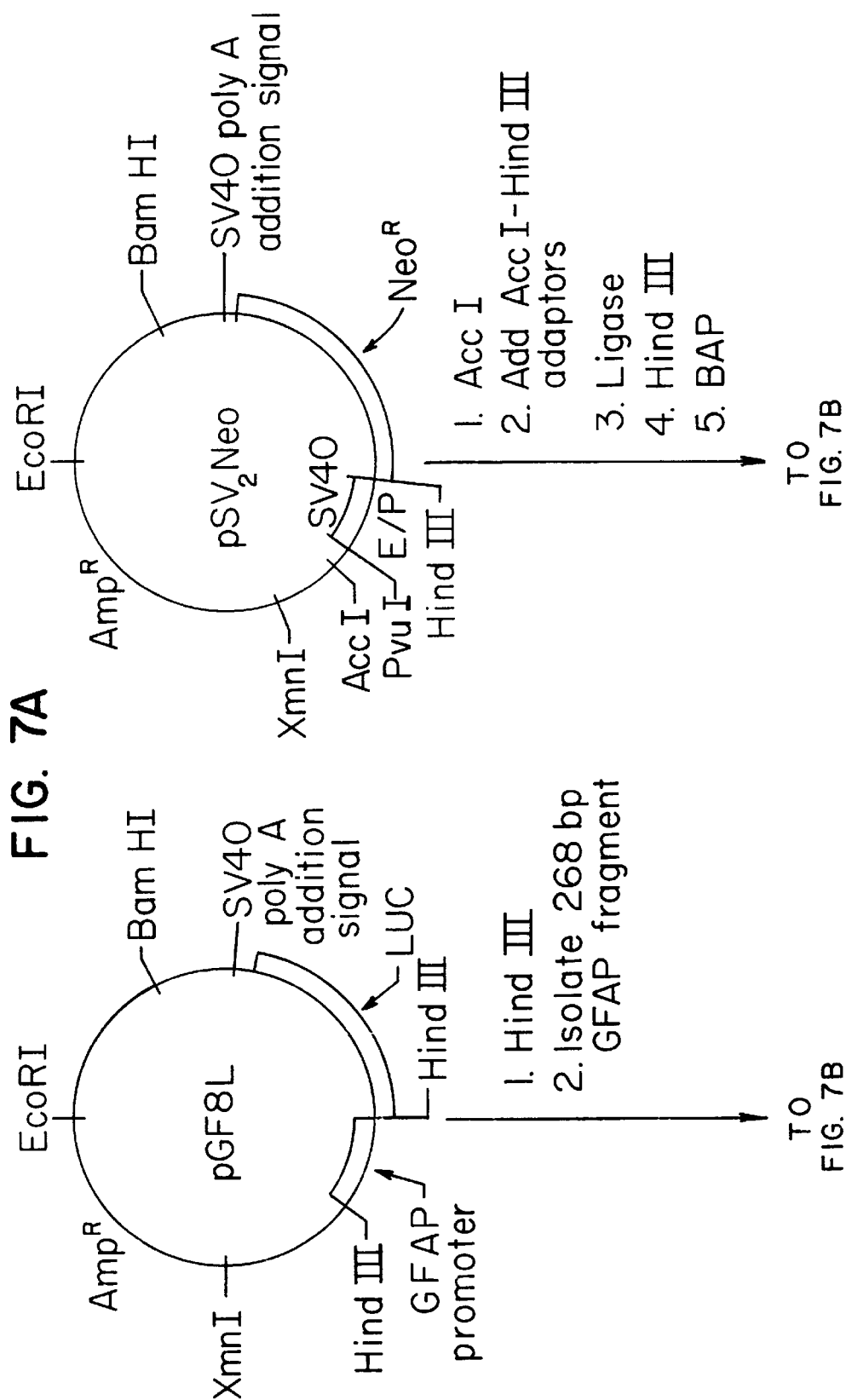

METHOD OF PRODUCING GENETICALLY MODIFIED ASTROCYTES AND USES THEREOF

This is a continuation, of application Ser. No. 07/909,281, filed Jul. 6, 1992, now abandoned.

This invention was made with support under Grant No. RR05736 of the National Institutes of Health. Accordingly, the U.S. Government has certain rights in the invention.

FIELD OF THE INVENTION

This invention relates in general to gene therapy, and more particularly to gene therapy utilizing genetically modified astrocytes. The astrocytes are genetically modified using non-viral transfection methods, such as a calcium phosphate procedure. This enables a foreign gene of interest to be expressed by the modified astrocyte in a human patient or animal subject, thereby being useful for gene therapy in the central nervous system. In addition, this technology can be utilized for prevention of illness and modification of normal neuroendocrine function, and can be packaged as a kit.

BACKGROUND OF THE INVENTION

Transplantation has become a major therapeutic option for a number of diseases over the past 20 years [Starzl et al., N Engl J Med 320:1014–1021,1092–1099 (1989); TINS 14(8):all pages (1991); Murray, Science 256:1411–1416 (1992)]. In fact, transplantation of many portions of the central nervous system has been achieved in rodents and other species, including animal models of nigrostriatal dysfunction related to Parkinson disease [Lindvall et al., Science 247:574–577 (1990); Goetz et al., New Engl J Med 320:337–341 (1989); Gill and Lund, J Am Med Assoc 261:2674–2676 (1990)].

Gage et al., in U.S. Pat. No. 5,082,670, issued Jan. 21, 1992, discloses the use of genetically modified (by means of retrovirus insertion of genes) fibroblast donor cells for grafting into the central nervous system (CNS) to treat diseased or damaged cells. The fibroblast donor cells can be modified to produce a protein molecule capable of affecting the recovery of cells in the CNS. The entire contents of U.S. Pat. No. 5,082,670 are hereby incorporated by reference into the subject application in order to more fully describe the state of the art of the subject invention.

Another cell which has been transplanted into the CNS is the astrocyte [Zhou et al., J Comp Neurol 292:320–330 (1990)]. Astrocytes have a wide range of functions, including: release of growth and trophic factors; inactivation of neurotransmitters; antigen presentation; ionic regulation; and response to certain lymphokines [Lillien and Raff, Neuron 5:111–1219 (1990); Raff, Science 243:1450–1455 (1989); Kimelberg and Norenberg, Scientific American, pp. 66–76 (April 1989)]. In addition, astrocytes from neonatal and adult sources (including human brain) replicate in vitro. Moreover, unlike fibroblasts, astrocytes belong in the brain and have region specific properties [Shinoda et al., Science 245:415–417 (1989); Batter and Kessler, Molec Brain Res 11:65–69 (1991)]. When transplanted, astrocytes survive at the site of injection and may migrate up to several millimeters into the host brain without forming tumors [Zhou et al. (1990)]. Some of the potential advantages of using astrocytes over skin fibroblasts concern this migration into the host brain, as well as lower epileptogenicity [Jennett, Arch Neurol 30:396–398 (1974)], and their natural expression of neurotransmitter receptors. Furthermore, although inadvertently displaced normal (primary) fibroblasts following spinal taps form spinal fibroma and transplants of established neuronal cell lines (e.g. C6-glioma, PC12 cells, etc.) often form neoplastic tumors, this has not occurred with astrocyte transplantation [Zhou et al. (1990); Emmett et al., Brain Res 447:223–233 (1988)]. Indeed, astrocytes only migrate away with little if any new cell division. In contrast, fibroblasts do not migrate and are limited by a reactive gliosis surrounding the transplant [Kawaja et al., J Comp Neurol 307:695–706 (1991)] while astrocytes can interdigitate between neurons after migration and thus have direct contact with neurons [Zhou et al. (1990)].

In addition to the choice of a particular cell for transplantation, a method for modifying the particular cell must also be chosen. A common method, such as the method disclosed in Gage et al., is viral-mediated gene transfer. Viral-mediated gene transfer raises safety issue problems due to the use of active and potentially pathogenic viruses [Amer Soc for Microbio News 58(2):67–69 (1992)]. For example, the biological properties of retroviruses utilized by Gage et al. have potential for causing mutations or cancer, and the possibility of continued infectivity. Furthermore, the physical dimensions of retroviruses limit the amount of foreign DNA which can be transferred via the retrovirus.

Another alternative method of gene transfer is chemical mediated gene transfer, such as by stable calcium phosphate transfection. The parameters for transfecting cells by this method vary for each different cell type, and therefore need to be determined and optimized for each different cell type.

SUMMARY OF THE INVENTION

It is thus an object of the subject invention to provide genetically modified normal (primary) astrocytes which can be utilized in gene therapy. It is a further object to provide such genetically modified astrocytes utilizing a chemical transfection means such as calcium phosphate transfection.

It is also an object of this invention to provide plasmids and various vectors for transfecting such astrocytes.

Also provided are methods of utilizing the genetically modified astrocytes, selecting for them, inducing the gene of interest, and a "poison pill" method, etc.

In accordance with these objectives, the invention provides genetically modified normal (primary) astrocytes which can be maintained in selective media for over one year or can be released to rapidly expand the population in vitro after at least three weeks of selection (see below). In such astrocytes, a stably incorporated expressed gene can be readily detected in vitro prior to transplantation. These cells can be identified in vivo following transplantation into the striatum for at least three weeks by Nissel staining, by GFAP staining, and by detection of the gene of interest (e.g. the reporter gene chloramphenicol acetyl transferase activity). Other methods of cell detection include PHAL lectins, microbeads, fluorescein dyes, and $^3$H-Thymidine. Furthermore, the expression of a transfected promoter construct (pENKAT12) can be regulated by dopaminergic receptor pathways in such astrocytes.

BRIEF DESCRIPTION OF THE FIGURES

These and other objects, features and advantages of this invention will be evident from the following detailed description of preferred embodiments when read in conjunction with the accompanying drawings in which:

FIGS. 6A and 6B illustrate the construction of plasmid PENKBASIC-B;

FIGS. 7A and 7B illustrate the construction of plasmid pGF8neo;

DETAILED DESCRIPTION OF THE INVENTION

MATERIALS AND METHODS

Plasmid Constructions

Figure 2:
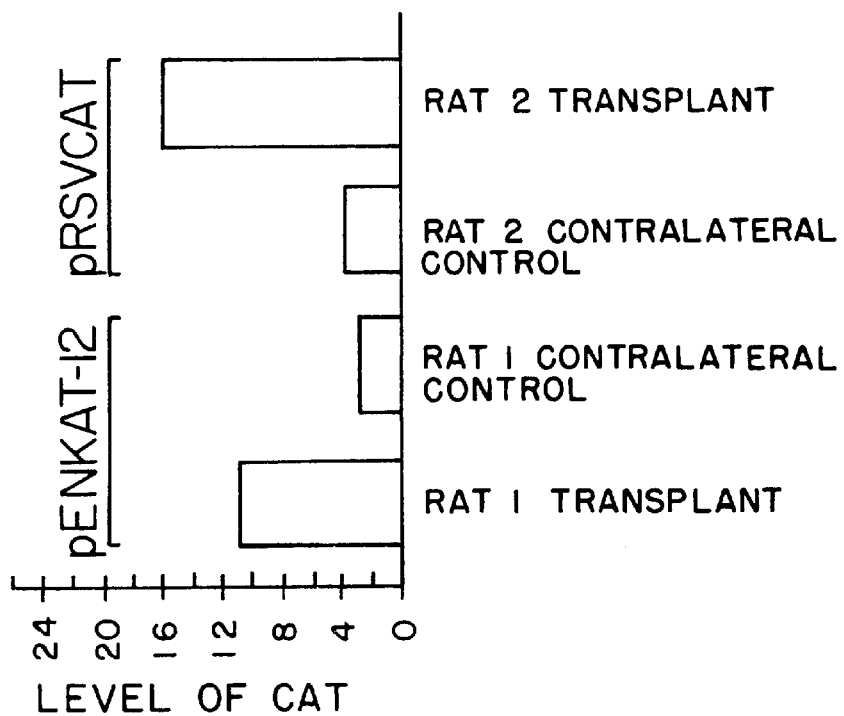
FIG. 2 illustrates CAT activity in vivo after transplant of stably transfected astrocytes.

All plasmids for use in development, prevention and therapeutic purposes were made using standard restriction enzyme modification, and other DNA isolation, preparation, and ligation as required. These standard methods are summarized by Ausubel et al., in Current Protocols in Molecular Biology, Wiley & Sons, New York, N.Y. (1992), and by Sambrook et al., in Molecular Cloning: A Laboratory Manual, 2nd ed., Cold Spring Harbor Press, Cold Spring Harbor, N.Y. (1989).

Site-specific DNA cleavage is performed by treating with the suitable restriction enzyme (or enzymes) under conditions which are generally understood in the art, and the particulars of which are specified by the manufacturer of these commercially available restriction enzymes. (See, e.g. New England Biolabs, Product Catalog.) In general, about 1 $\mu$g of plasmid or DNA sequences is cleaved by one unit of enzyme in about 20 $\mu$l of buffer solution. Typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid is recovered from aqueous fractions by precipitation with ethanol. If desired, size separation of the cleaved fragments may be performed by polyacrylamide gel or agarose gel electrophoresis using standard techniques. A general description of size separations is found in Current Protocols in Molecular Biology (1992).

Restriction cleaved fragments may be blunt ended by treating with the large fragment of *Escherichia coli* DNA polymerase I (Klenow) in the presence of the four deoxynucleotide triphosphates (dNTPs) using incubation times of about 15 to 25 minutes at 20° C. to 25° C. in 50 mM Tris (pH 7.6), 50 mM NaCl, 6 mM $MgCl_2$, 6 mM DTT and 5–10 $\mu$M dNTPs. The Klenow fragment fills in at 5' sticky ends but chews back protruding 3' single strands, even though the four dNTPs are present. A more efficient method of chewing back protruding 3' overhangs is by using T4 DNA polymerase instead of the Klenow fragment. After treatment with Klenow or T4 DNA polymerase, the mixture is extracted with phenol/chloroform and ethanol precipitated. Treatment under appropriate conditions with S1 nuclease or Bal-31 results in hydrolysis of any single-stranded portion.

Ligations are performed in 15–50 $\mu$l volumes under the following standard conditions and temperatures: 20 mM Tris-Cl pH 7.5, 10 mM $MgCl_2$, 10 mM DTT, 33 mg/ml BSA, 10 mM–50 mM NaCl, and either 40 $\mu$M ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt-end" ligation). Intermolecular "sticky end" ligations are usually performed at 33–100 $\mu$g/ml total DNA concentrations (5–100 nM total end concentration). Intermolecular blunt end ligations (which can be performed employing a 5–30 fold molar excess of linkers) are performed at 1 $\mu$M total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of $Na^+$ and $Mg^{+2}$ using about 1 unit of BAP or CIP per mg of vector at 55 to 60° C. for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Culturing of Rat Astrocytes:

Two day old Sprague Dawley rat pups were sacrificed by decapitation. After the skull was opened and the brain removed, it was placed in CMF-Sal G (calcium magnesium free P-SAL G) in a culture dish on ice [Vilijn et al., Proc Natl Acad Sci USA 85:6551–6555 (1988)]. Striata from ten animals were microdissected to seed approximately 30 (1.5 ml) dishes at $5 \times 10^5$ cells per dish. This tissue was minced with forceps, transferred to a 15 ml sterile conical tube, and the supernatant that remained after momentary settling was used to rinse the culture plate. The tissue was then centrifuged (500–1000×g, 1 minute), the supernatant was aspirated off, and the cells were resuspended in 2 ml of 0.1% trypsin (1.0% Gibco #610–5095AE diluted 1:10 v/v with CMF-Sal G) and allowed to incubate for 30 minutes at 37° C. Incubation was followed by recentrifugation (500–1000× g, 1 minute) and resuspension of the pellet in 2 ml of complete media by gentle trituration until a uniform suspension was seen. The cells were plated at a density ratio of $5 \times 10^5$ cells per 1.5 ml of complete media (swirled gently) on poly-D-lysine (Sigma #P7886, pH 8.5) coated plates (35 mm dish, Falcon #3001) ($1.0 \times 10^6$/10 ml for 100 mm dish, Falcon #3003) and incubated at 37° C., 100% relative humidity and 5% $CO_2$, for five to six days. The media was then replaced with ice cold media (1.5 ml for 35 mm dish; or 10 ml for 100 mm dish) and the dishes were agitated to remove neural non-adherent cells [Vilijn et al. (1988)]. Subsequently, the media (37° C.) was changed every 4 to 5 days, until the cells grew to confluency (about two weeks), and then the cells were passaged every 3 weeks using trypsin (see below) to release the cells from the poly-D-lysine coated plates. At this point, the cells were either used for transfection or for primary culture experiments.

Identity of the astrocyte cells was validated by glial fibrillary acidic protein (GFAP) staining and morphology. Astrocytes at low density have star-like shapes and are very flat; at high density they form a "cobble-stone" pattern. Neurons, on the contrary, have long processes (neurofilaments), and are less than 1% of the cells. Fibroblasts look very similar to astrocytes, but are GFAP negative. Oligodendrocytes are dark cells with short processes which are much smaller than astrocytes and sit on the surface of the astrocytes. Using the above-described protocol, over 95% of the astrocyte cells were GFAP positive.

Replating Protocol

Cells are replated by placing 2–3 ml of Serum Free Medium or PBS×2 in each 100 mm plate and adding 0.05% Trypsin-EDTA, Gibco #610–5300Af [0.5 ml in 1.5 ml Dish (30 mm); 1.0 ml in 5 ml Dish (60 mm); 2.0 ml in 10 ml Dish (100 mm)]. Incubate at 37° C. for 5 minutes, then tap culture dish 25 times to release rounded up cells. Pool samples and add 1:1 (v/v) media with serum. Centrifuge for 5 minutes at 1000 rpm (500–1000 g). At this point, consider repeating trypsin treatment of the original plates. Then resuspend the cells in an appropriate volume and count an aliquot. Replate at about $0.5 \times 10^6$/30 mm Dish, $1.0 \times 10^6$/60 mm Dish, or $2.0 \times 10^6$/100 mm Dish (or one-half this amount for transfection).

Cell Handling After Transfection: Near confluent astrocyte cultures were replated at $1 \times 10^6$ cells per 100 mm culture dish, and then plasmids (pRSVCAT or pENKAT12, 10 μg) were introduced into astrocytes by the calcium phosphate transfection procedure. Stably transfected cells (see next section) were developed by co-transfection of 10–15 μg of a promoter reporter ("gene of interest") and 3 μg of pMCINeo PolyA (Stratagene) (or equivalently pRSVNEO) followed by glycerol shock 6–7 hours later. Then the media covering the cells was changed to selective media 16–18 hours later. The cells were then maintained for at least 3 weeks in selective medium containing G418 (300 μg/ml; note—100% mortality of cells which do not contain a resistance gene occurs at less than 200 μg/ml G418 within 14 days). G418-resistant astrocytes were grown in culture for at least 3 additional weeks without selective pressure prior to transplantation. A portion of stably transfected cells were harvested and lysates assayed for CAT enzyme activity [Gorman et al., Molecular Cellular Biology 2:1044–1051 (1982)]. Remaining cells were used for transplantation.

Following transfection of primary astrocytes with pRSVCAT, approximately 5% of cells were immunoreactive to the CAT protein with variable intensity of staining prior to selective pressure (e.g. after 24–48 hours). After selective pressure was applied, CAT positive cells are seen. At this stage 100% of cells are of this phenotype.

Figure 1:
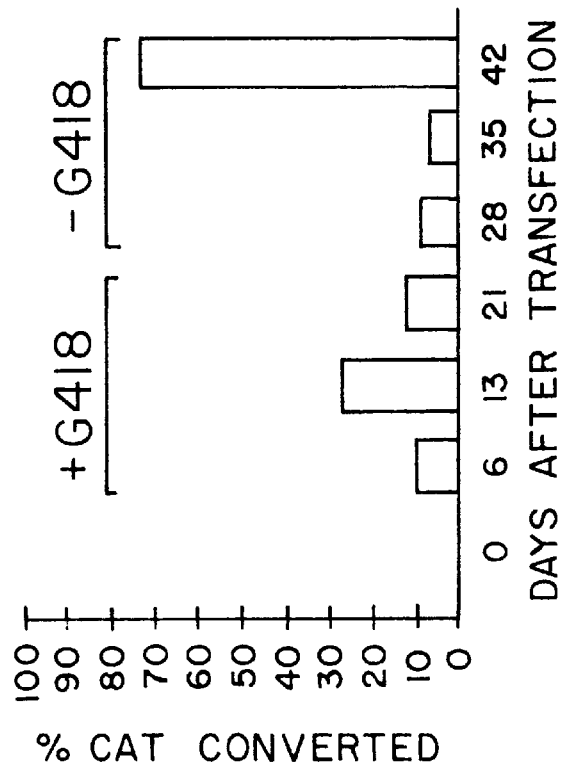
FIG. 1 illustrates CAT activity for transfected astrocytes in the presence and absence of selective pressure in vitro.

FIG. 1 illustrates CAT bioactivity during and after the release of selective pressure in vitro. Astrocytes were transfected, maintained in selective medium for 3 weeks, and released from selective pressure for 3 more weeks. Transfected astrocytes were harvested at the time points indicated. The marked rise in CAT activity at 42 days was associated with a dramatic rise in the number of astrocyte cells per dish in the absence of selective pressure. Stably transfected astrocytes have been maintained in culture with selective pressure for over one year. These results indicate that stably transfected astrocytes can maintain expression of the RSVCAT gene product for at least 3 weeks in vitro without selective pressure and can be maintained in culture for at least one year with selective pressure. This situation is similar to the absence of selective pressure that exists in vivo after short term transplantation.

Calcium Phosphate Transfection Protocol

Add DNA sequentially to 1 ml HeBS buffer [137 mM NaCl; 5 mM KCl; 0.7 mM $Na_2HPO_4$; 6 mM dextrose; 21 mM HEBS (pH 7.1)] in snap cap sterile polypropylene tubes (12×75 mm; Falcon #2063). For stables (ratio 4/1 or 5/1), add 15 μg of test plasmid in TE Buffer, then add 3.0 μg pMCINeo PolyA in TE Buffer (Stratgene, Inc.)(or pRSVNeo) and mix. For transients, use 10–15 μg of plasmid.

Then add 62.5 μl of 2M $CaCl_2$ and wait 30 minutes or less to allow fine crystals to form (tiny dots will be seen under a microscope, not clumps; excess time results in larger crystals which are less efficient in getting into the cells). During the crystal forming stage, wash culture plates with media minus serum two times (e.g. ½ vol of dish or about 5 ml) and aspirate to nearly dry. Note that plates were seeded on the previous day with $10^6$ cells per 10 ml dish.

At 30 minutes, add 1.062 ml $CaPO_4$/DNA precipitate mix to the center of the plate on a level surface (avoid bubbles on the plate), and wait 30 minutes (swirl every 10 minutes to keep monolayer wet) at about 37° C. for astrocytes. After 30 minutes, gently add 10 ml of complete media dropwise to slow stream to avoid dislodging cells.

At this point, wait 6 to 7 hours, then remove media until nearly dry. Glycerol shock cells by adding 2 ml of HeBS Buffer (15% glycerol) per dish for 90 seconds (should kill approximately 75% of cells). Then aspirate off and wash by adding media minus serum (dropwise, e.g. 5 ml for 10 ml plate or ½ volume of plate); rotate plate to rinse corners. Aspirate media off again, and then add 10 ml of complete media (dropwise, gently) to the center of the plate. The following day add the G418 antibiotic (12–18 hours may be best) at a G418 final concentration of 300 μg/ml (final) in HEPES. For example, add 100 μl per 10 ml of 30 mg/ml G418 solution. To facilitate regrowth, release selection after 3 weeks (e.g. no more G418). Prior to release change media every 4–5 days. Replate when the cells are 90% confluent.

Transplant Protocol: All surgical procedures are performed aseptically under equithesin anesthesia (a mixture of chloral hydrate and sodium pentobarbitol at 50/50 v/v), after placement of a small burr hole. Recipient rats received a 5 μl injection of 30,000 to 500,000 cells in PBS with or without 33 mM glucose injected through a 10 μl Hamilton microsyringe (18 or 25 Gauge needle). The needle is positioned stereotaxically into the left or right striatum and each injection is made over 3 minutes. Following injections, the needle was left in place for 1 minute before slow withdrawal. Sham grafts (negative controls) consisted of an equal volume of saline or untransfected astrocytes injected in the same manner.

CAT Assay: Tissue is harvested for assay of CAT enzyme activity by dissecting the brain region with the transplant (tissue block of 2×2×4 mm around transplant, a border of about 1–2 mm, approximately 50 mg tissue). Freeze on dry ice and pulverize in porcelin mortar on liquid nitrogen. Rinse fragments into Eppendorf with liquid nitrogen allowing it to evaporate on dry ice. Add 70 μl of 0.25 M Tris (pH 7.8) and cycle to 37° C. then −70° C. three times. Recover a 50 μl supernate aliquot (after centrifuging) into a clean tube. Then mix sequentially 34 μl $ddH_2O$, 70 μl 1 M Tris (pH 7.8), 25 μl extract, and 1 μl of $C^{14}$-chloramphenicol (0.1 μCi/tube). Pre-incubate tubes at 37° C. for 5 minutes. Then add 20 μl Acetyl CoA (4 mM, lithium salt) and incubate for 60 minutes at 37° C. Extract with 1 ml ethyl acetate by collecting upper organic layer (vortex 30 seconds, microcentrifuge 30 seconds). Dry, then resuspend in 25 μl ethyl acetate, spot and separate on TLC (thin layer chromatography) plates (Chromagram #13179, Eastman Kodak—no fluorescence) in 95/5 v/v chloroform/methanol for two hours. Dry plates, coat with C14 enhancer (e.g. with Resolution by EM Corp.), allow to dry, and then expose autoradiograph for 2 days or longer (at −80° C. with fluorescent screen) before analyzing by densitometer for quantitation, or scintillation counting for quantitation.

FIG. 2 provides evidence that the CAT gene is expressed in the brain after transplant of stably selected transfected astrocytes. CAT activity was detected 3 weeks after transplantation of stably transfected astrocytes in the appropriate hemisphere. CAT enzyme activity was not affected by the presence of brain tissue in the extract.

Histology: Rats were perfused transcardially under deep equithesin anesthesia with 4% paraformaldahyde in 0.1 M phosphate buffer. Fixation was continued for 2–24 hours, followed by cryoprotection in graded 10–30% sucrose in the same buffer, freezing on dry ice, and cryostat sectioning at 30 μm. Coverslips were fixed in the same solution for 10 minutes or methanol:acetone 1:1 for 2 minutes. Freefloating sections and coverslip were washed in 0.1M phosphate buffered saline pH 7.2–7.4 (PBS), treated with 0.2% TritonX-100 for 30 minutes. Primary antibodies were rabbit anti-chloramphenicol acetyltransferase (CAT) antibody, 1:10 to 1:20,000 (5 Prime–3 Prime, Inc., Boulder, Colo.), Histogen GFAP monoclonal antibody (Biogenex Labs, San Ramon, Calif.) and beta-Gal antibody, 1:500 to 1:2,000. Each was diluted in PBS containing 3% goat serum and 0.3% TritonX-100. Antibody binding was visualized with Vectastain ABC (Vector Labs, Burlingame, Calif.) and diaminobenzidine. Control sections were reacted with the primary antibody omitted or replaced with an unrelated antibody. Adjacent sections were mounted serially and stained with cresyl violet.

Transient Transfection of Astrocytes For Rapid Drug Assay—Receptor Evaluation

Following transient transfection with plasmid pENKAT12 [Comb et al. (1986)] without a Neo gene plasmid [Graham and Van der Eb, Virology 53:456–457 (1973); Weisinger et al., Oncogene 3:635–646 (1988)], astrocytes were treated with drugs (see below). On harvest, the cell lysates were assayed for CAT expression (the transfected reporter gene, a bacterial gene not present in eukaryotes) [Gorman et al. (1982); Weisinger et al. (1988)]. Transfection efficiencies were standardized by Southern analysis of plasmid DNA in Hirt lysates [Hirt, J Mol Biol 26:365–369 (1967); Weisinger et al. (1988)].

To quantitate CAT activity, 20 μl of each cell lysate was used to acetylate [$^{14}$C]chloramphenicol [Lopata et al., Nuc Acids Res 12:5707–5717 (1984); Weisinger et al. (1988)] (see protocol above). Chloramphenicol and its acetylated derivatives were separated by ascending silica gel thin layer chromatography ($CHCl_3:CH_3OH$, 95:5 v:v), visualized by autoradiography [Weisinger et al. (1988)], and analyzed with a densitometer (see above details) or by scintillation counting of TLC spots.

For RNA analysis, total RNA was prepared by the acid guanidinium thiocyanate/phenol/chloroform method of Chomczynski and Sacchi [Chomczynski and Sacchi, Anal Biochem 162:156–159 (1987)], as modified [Weisinger et al., J Biol Chem 265:17389–17392 (1990); LaGamma et al. Molec Br Res 13:189–197 (1992)]. Total RNA was quantified by optical density and 10 μg aliquots were fractionated on 1% glyoxal gels and transferred to Nytran (S&S) or nylon Biotrans (ICN) membranes. Northern blot prehybridization and hybridization solutions were as previously described [LaGamma et al. 1992]. Briefly, each RNA blot was hybridized at 45° C. to a radiolabelled double stranded coding region fragment of ppEnk cDNA (pRPE2) or glyceraldehyde-3-phosphate dehydrogenase (pRGAPDH-13) for 24–48 hours. A PvuII digest of plasmid pRPE2 [Yoshikawa et al., J Biol Chem 259:14301–14308 (1984)] yielded a 435 bp exon 3 fragment, which was labelled with $^{32}$P-dCTP using random primer labelling kits (Prime-it; Stratagene).

Blots were rehybridized to a PstI 1,085 bp fragment of pRGAPDH-13 [Piechaczyk et al., Nuc Acids Res 12:6951–6963 (1984)] as an RNA loading control. Following each hybridization, the blots were washed at 60° C. in 0.2xSSC/0.1% SDS for 30 minutes and again at 50° C. and then autoradiographed.

Evaluation of drug treatments were performed after plasmid pENKAT12 [Comb et al. (1986)] was introduced into the cells. The day after the transient transfection, the cultures were treated with either dopaminergic or serotonergic drugs at various concentrations for a further 16–18 hours. Following drug treatment the cultures were then harvested, and cell extracts were made and assayed for both chloramphenicol acetyl transferase (CAT) activity and levels of transfected plasmid (Hirt lysates) as discussed above, or for endogenous RNA levels.

All drugs were made up in sterile PBS and then resterilized through Acrodisc13 (0.2 μm; GelmanSciences) and added to each 1.5 ml culture in a final volume of 0.1 ml. Dopamine-HCl, Apomorphine-HCl, SKF38393-R(+), Ly17155, SCH39166, s(−)-Sulpiride, Serotonin-HCl, 5-methoxytryptamine and Buspirone were purchased from Research Biochemicals Inc. (Massachusetts). In the combined drug experiments both drugs were added simultaneously and maintained for the entire 16–18 hours. Following harvesting and extraction, CAT assays were run (see above).

Autoradiograms were quantified by two dimensional scanning densitometry using a LKB 2400 Gelscan XL (Bromma, Sweden). Digitized data were analyzed with LKB Gelscan software (version 1.0) on an IBM AT computer, as previously described [Weisinger et al. (1990)]. Multiple autoradiogram exposures of the same experiments were analyzed so that band or spot intensities reported represented sub-saturation values. One-way analysis of variance was performed on the data, followed by Newman-Keuls test, where appropriate [Zar, in Biostatistical Analysis, pp. 101–162, Prentice-Hall, N.J. (1974)].

EXAMPLE 1

Construction of Plasmid pENKTH2

Figure 3A:
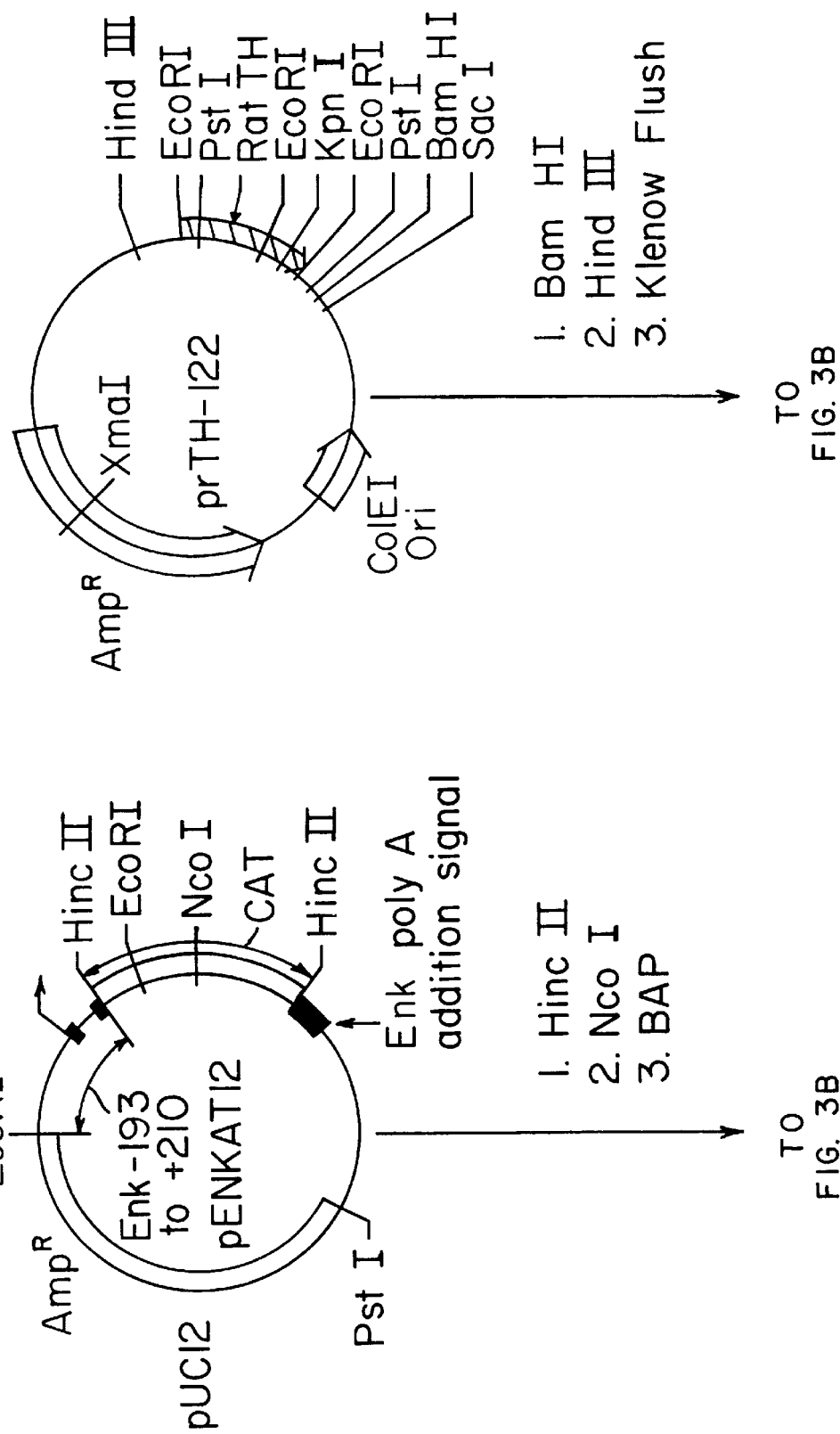
FIGS. 3A and 3B illustrate the construction of plasmid pENKTH2.
Figure 3B:
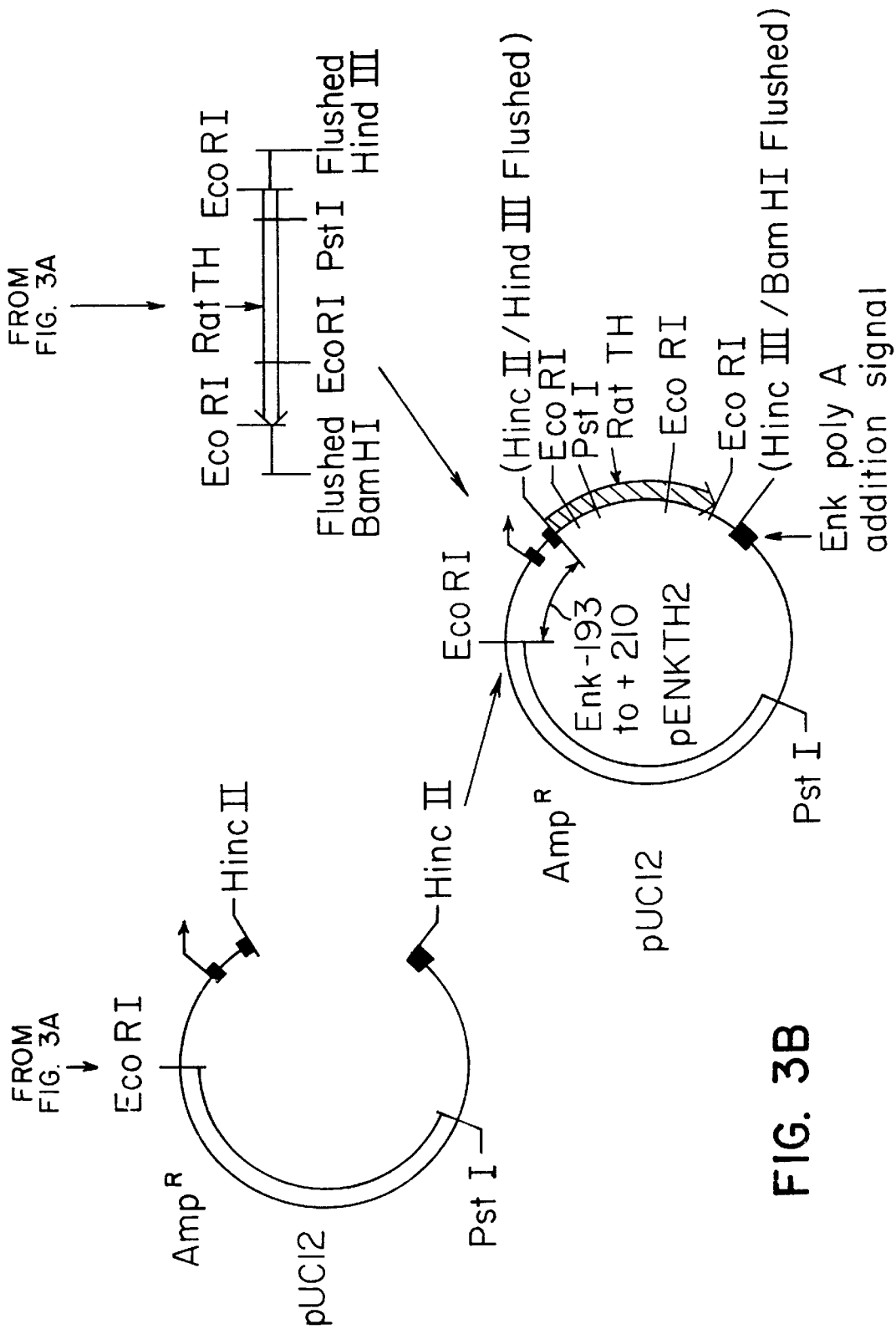

Referring to FIG. 3, plasmid pENKAT12 (Comb et al. 1986) was restricted using HincII followed by NcoI. This linearized plasmid was then treated with bacterial alkaline phosphatase (BAP) twice, in order to remove the 5' phosphate and prevent future religation of the vector on itself. A 1900 base pair BamHI-HindIII DNA fragment containing the rat tyrosine hydroxylase from the prTH122 plasmid (supplied by Dr. K. O'Malley, Washington University, St. Louis, Mo.) after having its 5' overhangs flushed using the Klenow fragment of *Escherichia coli* polymerase, was ligated into the HincII backbone of the above linearized pENKAT12. pENKTH2 was the resultant form that allowed sense rat tyrosine hydroxylase transcription from the human preproenkephalin gene promoter.

Application of Plasmid pENKTH2

This vector will allow expression of the tyrosine hydroxylase gene product in astrocytes for use in animal models of Parkinson's disease or in human therapy for Parkinson's disease, where increased activity of this tyrosine hydroxylase enzyme can produce dopamine and alleviate functional deficits.

EXAMPLE 2

Construction of Plasmid pENKHTH1

Figure 4A:
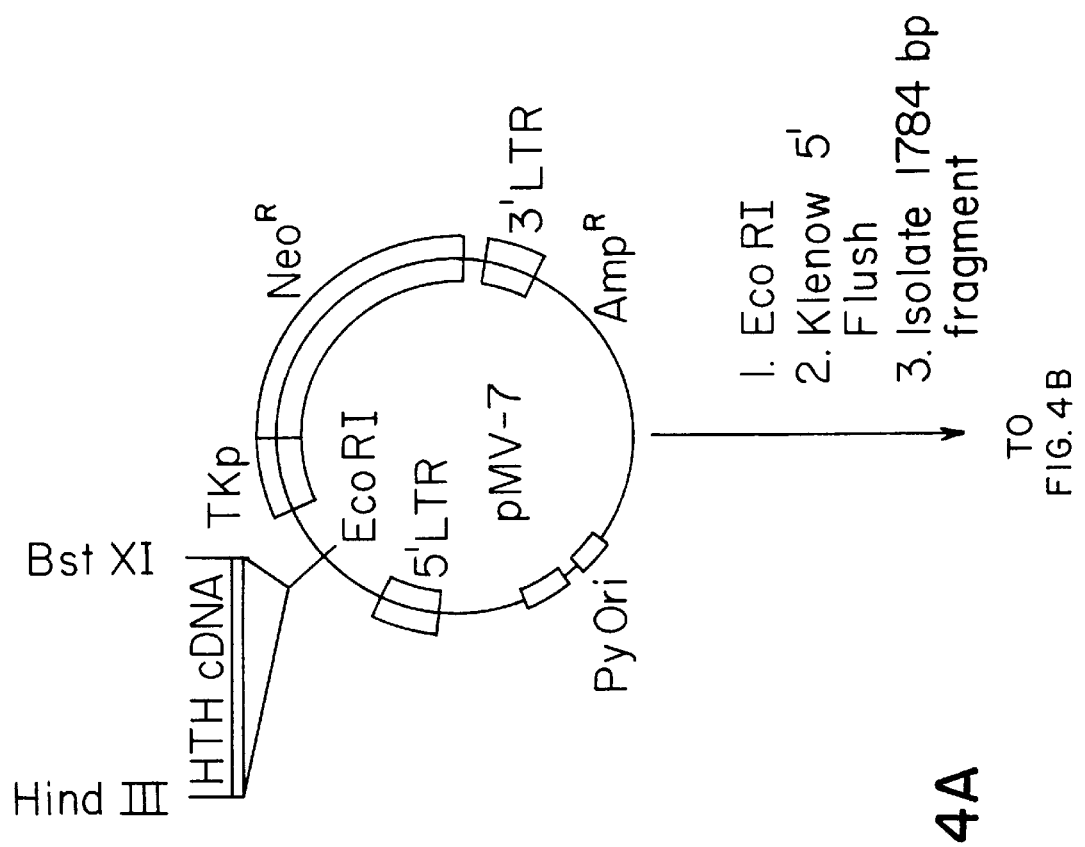
FIGS. 4A and 4B illustrate the construction of plasmid pENKHTH1.
Figure 4A:
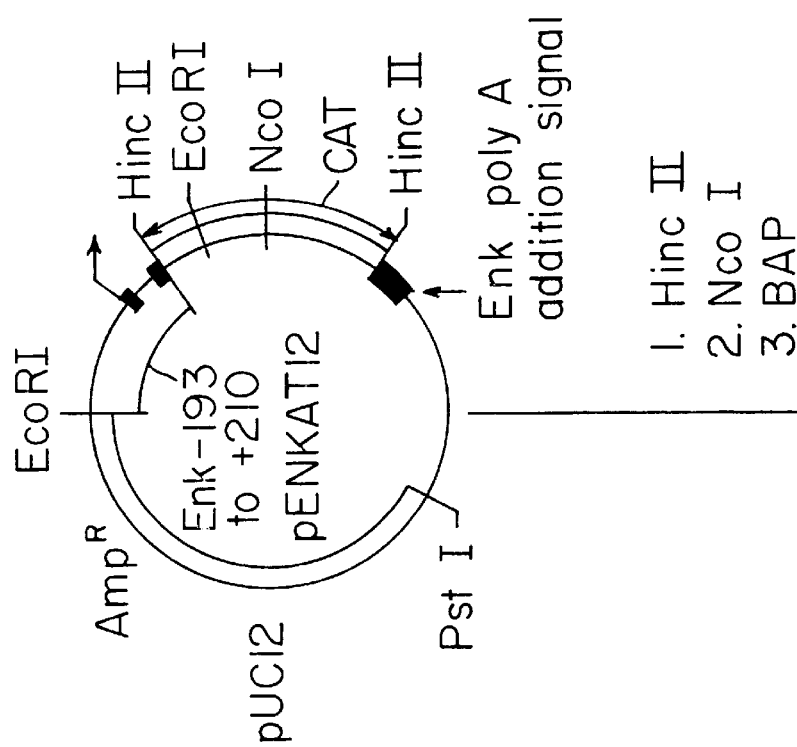
Figure 4B:
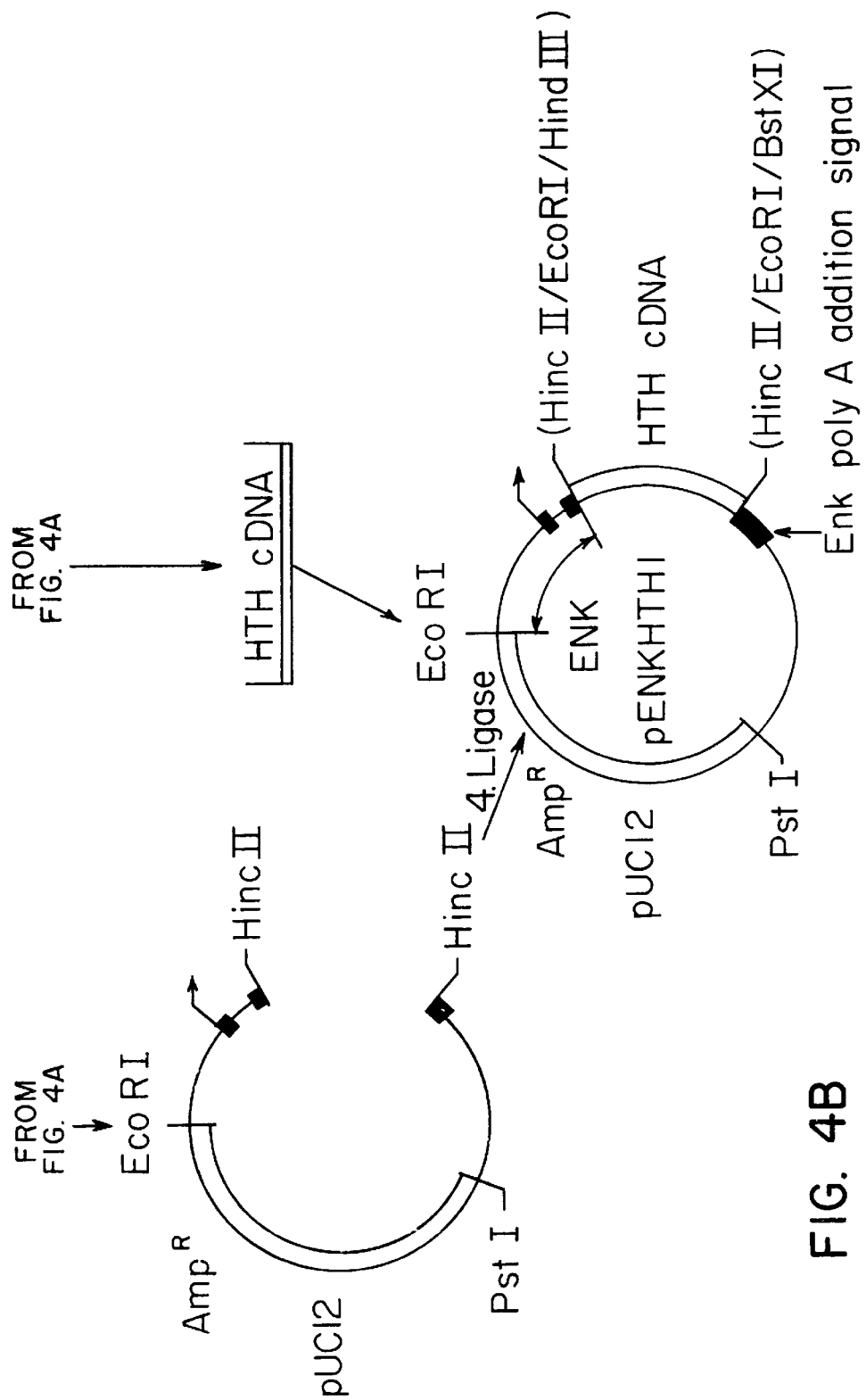

Referring to FIG. 4, a 1784 base pair EcoRI fragment derived from pMV-7 [Horellou et al., Proc Natl Acad Sci USA 86:7233–7237 (1989)], containing the human tyrosine hydroxylase gene (HindIII-BstXI fragment) was isolated and had its EcoRI 5' overhangs flushed using the Klenow fragment of *Escherichia coli* polymerase. This fragment was then ligated into the HincII backbone of the above linearized pENKAT12. The correctly oriented form of this plasmid was selected such that sense transcription of the human tyrosine hydroxylase gene was generated following RNA initiation at the human preproenkephalin promoter. This plasmid was designated pENKHTH1.

Application of Plasmid pENKTH1

This vector differs from pENKTH2 only in that the human tyrosine hydroxylase (TH) gene is expressed. The usefulness of TH expression in Parkinson's therapy is similar to that discussed for plasmid pENKTH2 above.

EXAMPLE 3

Construction of Plasmids pENKBASIC and pENKBASIC-B

Figure 5A:
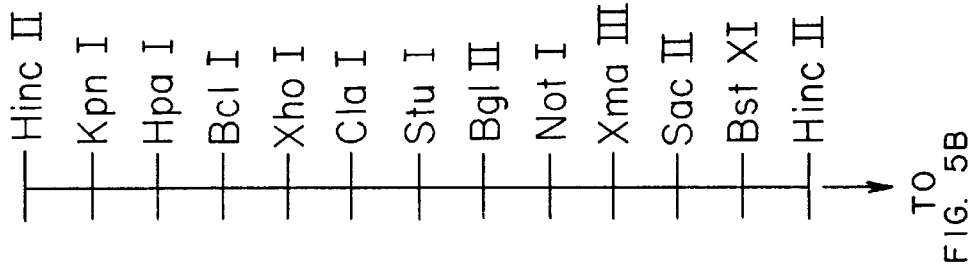
FIGS. 5A and 5B illustrate the construction of plasmid pENKBASIC.
Figure 5A:
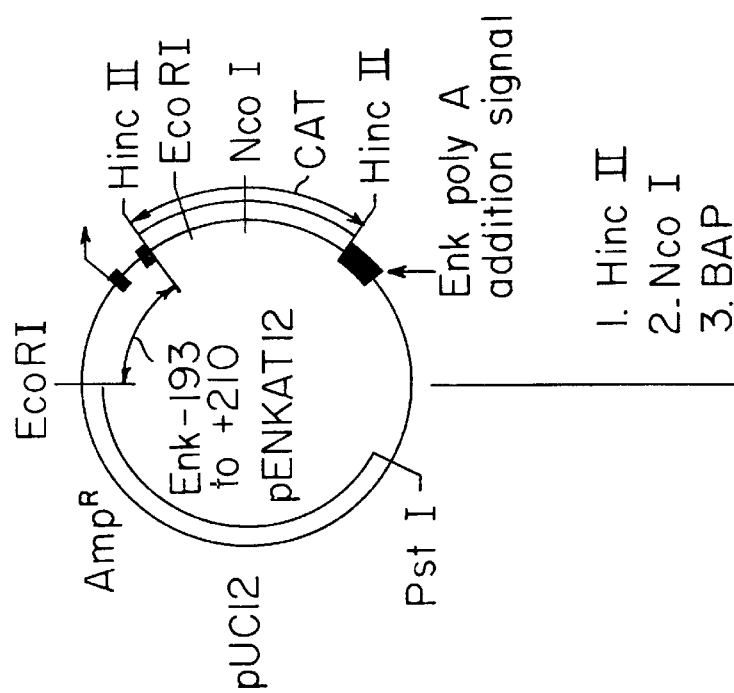
Figure 5B:
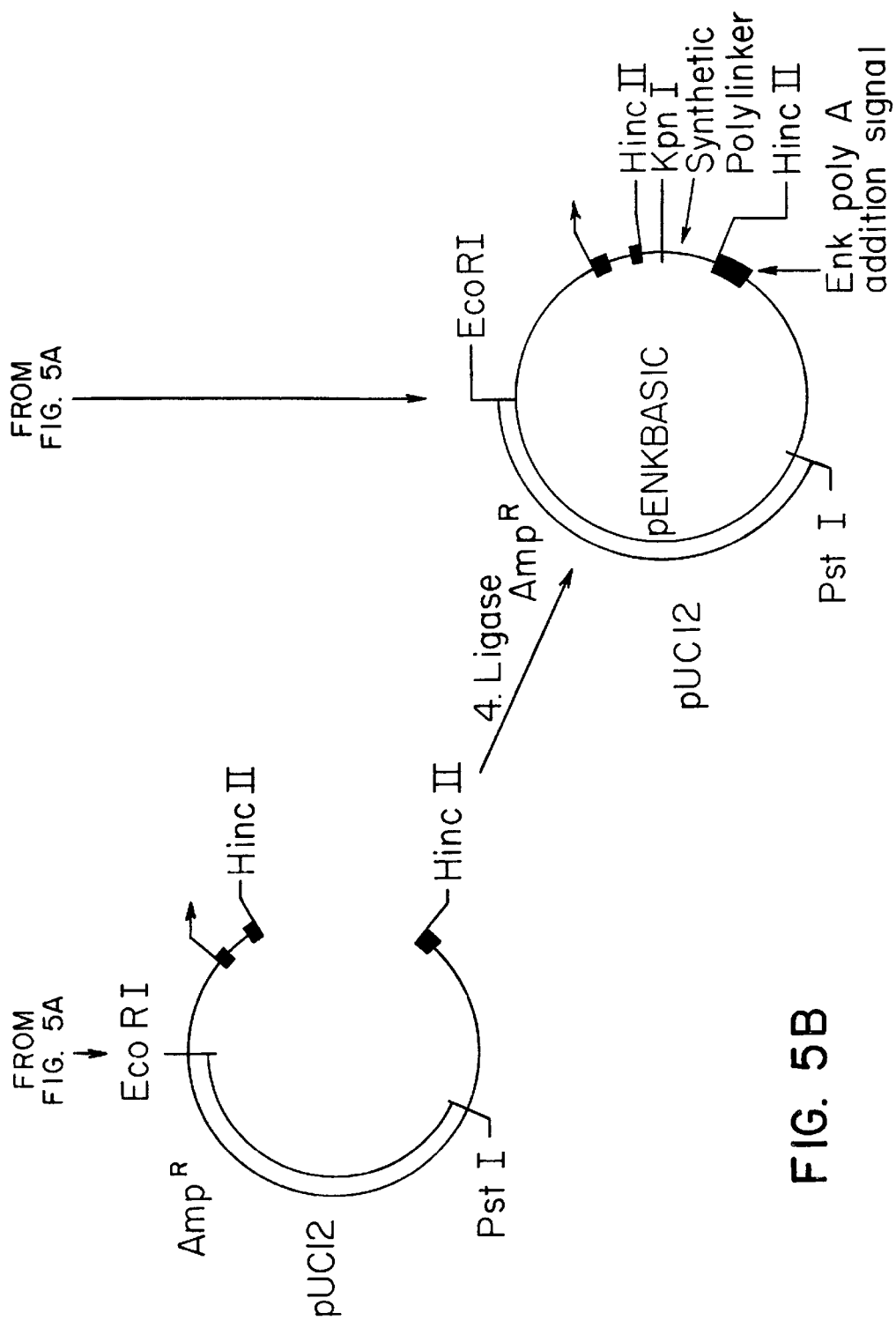
Figure 6B:
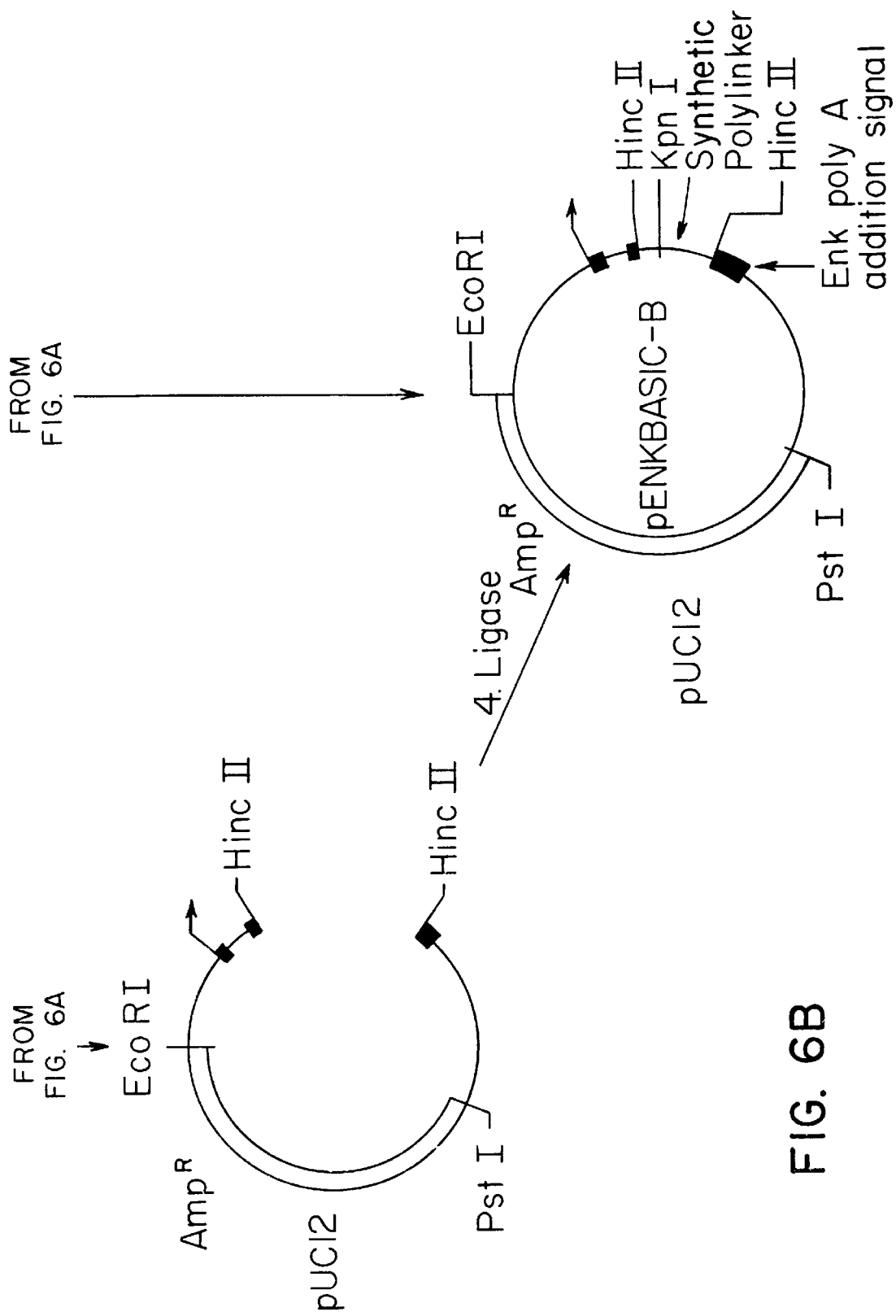

Plasmids pENKBASIC and pENKBASIC-B had double stranded synthetic custom polylinkers with HincII ends ligated into the same HincII restricted, BAP treated pENKAT12 backbone used in the previous two constructs. Both polylinkers had 11 unique 6 mer or better unique restriction enzyme recognition sites between two HincII sites. The pENKBASIC polylinker had the following set of restriction sites: HincII, KpnI, HpaI, BclI, XhoI, ClaI, StuI, BglII, NotI, XmaIII, SacII, BstXI, HincII. The pENKBASIC-B polylinker has the following set of restriction sites: HincII, KpnI, HpaI, BclI, XhoI, SmaI/ApaI, PstI, BglII, NotI, PvuI, SacI, SphI, HincII. Each vector is designated with a "+" or "−" depended on the orientation of the polylinker, with respect to the preproenkephalin promoter (see FIGS. 5 and 6).

Application of Plasmids pENKBASIC and pENKBASIC-B

These generic vectors will allow any gene of interest to be expressed and regulated by the human enkephalin promoter. The polylinkers facilitate the insertion of any coding region sequence into the splice site.

EXAMPLE 4

Construction of Plasmid pGF8neo

Figure 7B:
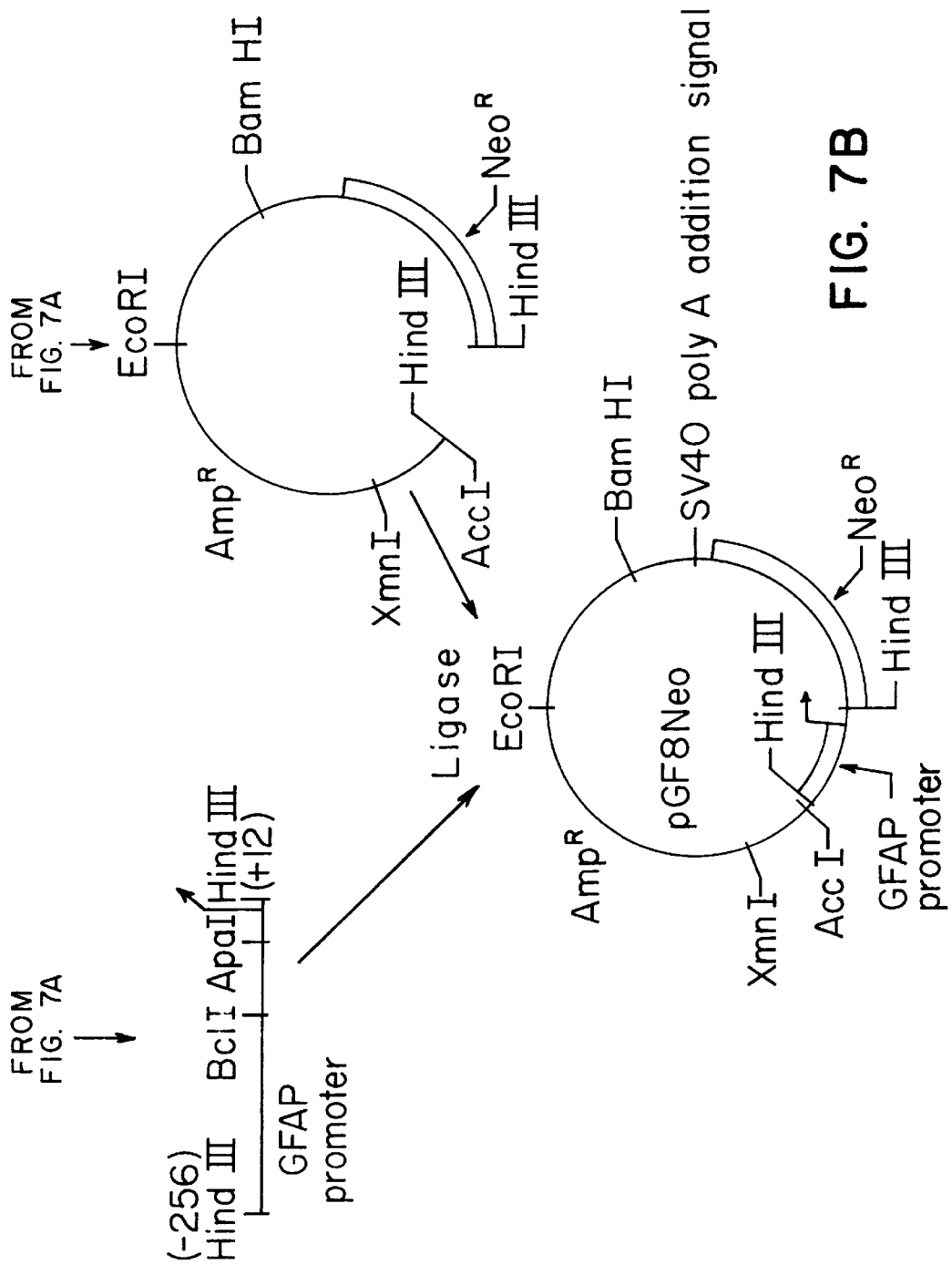

Referring to FIG. 7, the plasmid pSV$_2$neo (commercially available from the ATCC—American Type Culture Collection, 12301 Parklawn Drive, Rockville, Md. 20852 U.S.A.) was restricted with AccI and treated twice with BAP. AccI-HindIII adaptor fragments were ligated into the above linearized pSV$_2$neo to make pSV$_2$Hneo. This plasmid was then further restricted with HindIII and again treated twice with BAP. Into this linearized plasmid a 268 base pair GFAP promoter containing HindIII fragment was ligated. This GFAP fragment was HindIII restricted from the plasmid pGF8L [Miura et al., J Neurochem 55:1180–1188 (1990)]. Only the plasmid with the GFAP promoter driving a sense neo gene was designated pGF8neo.

Application of Plasmid pGF8neo

For an application of plasmid pGF8neo, see details below concerning the "poison pill".

EXAMPLE 5

The effects of dopaminergic and serotonergic receptor agonists and antagonists in cultures of primary rat astrocytes were examined. Astrocytes were transiently transfected with a chimeric human preproenkephalin promoter (human ppEnk)-bacterial chloramphenicol acetyl transferase plasmid (pENKAT12 of Comb et al. [Comb et al., Nature 323:353–356 (1986)] and treated with different dopaminergic and serotonergic drugs. The resulting agonist induced effects were compared to the effects on the endogenous rat ppEnk gene (under control of the endogenous rat ppEnk promoter) in replicate cultures. The dopaminergic agonists were found to induce a response in the transfected pENKAT12 plasmid while serotonergic agonists did not. Furthermore, while there was a dopaminergic induction of expression of the transfected gene under control of the human ppEnk promoter, there was only a marginal effect on the induction of the endogenous rat ppEnk promoter.

Figure 8:
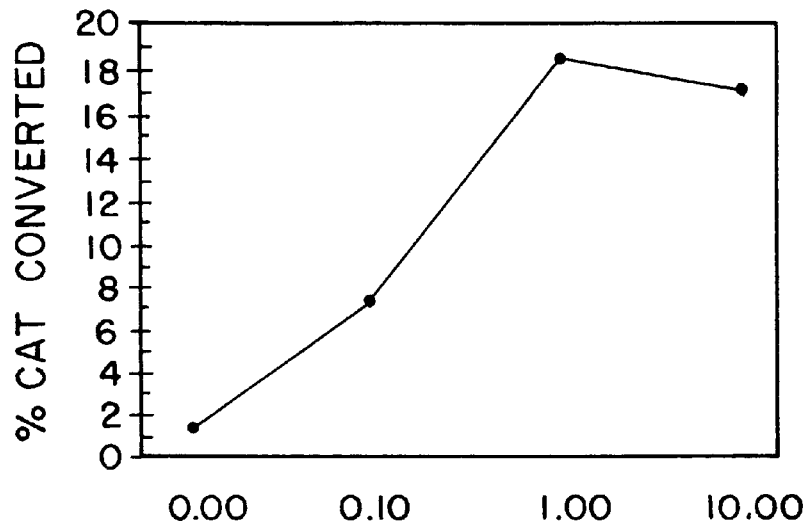
FIG. 8 is a dose response curve for dopamine on the inducability of pENKAT12 in cultured rat astrocytes.
Figure 9:
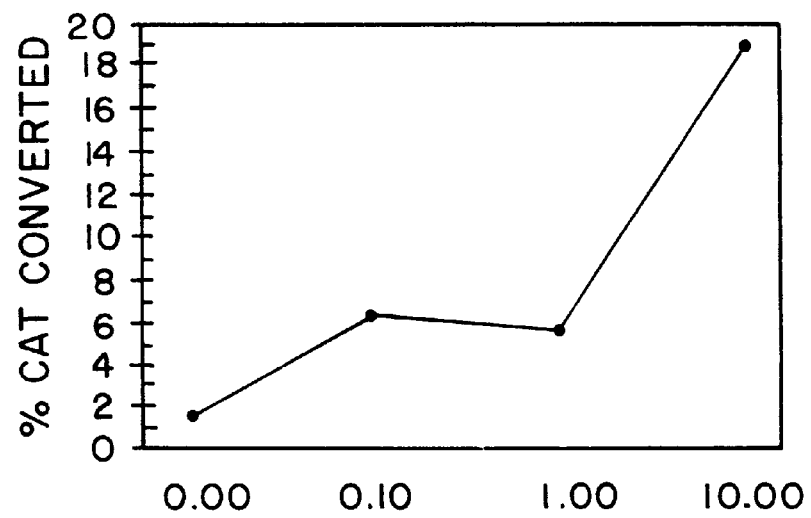
FIG. 9 is a dose response curve for apomorphine on the inducability of pENKAT12 in cultured rat astrocytes.
Figure 10:
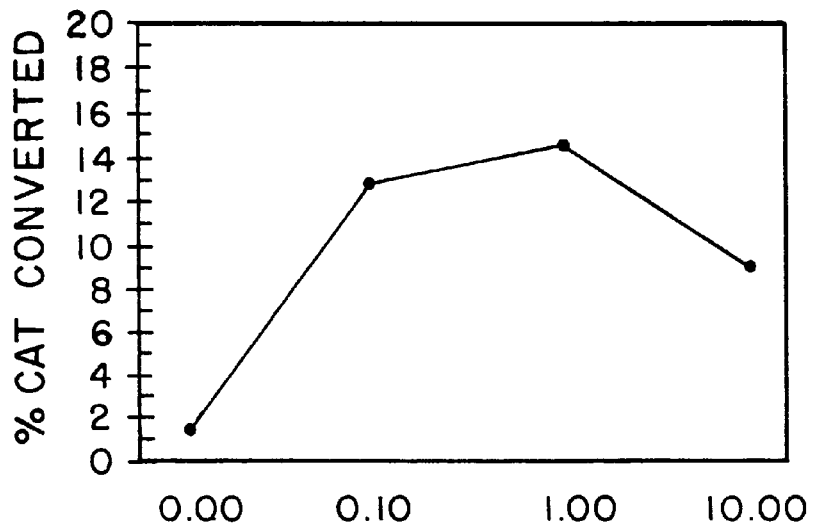
FIG. 10 is a dose response curve for SKF38393-R(+) (D1-receptor agonist) on the inducability of pENKAT12 in cultured rat astrocytes.
Figure 11:
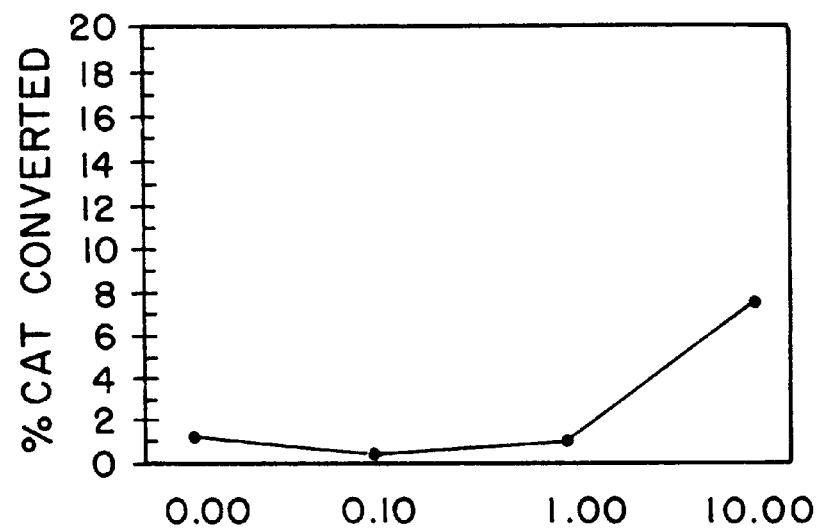
FIG. 11 is a dose response curve for LY17155 (D2-receptor agonist) on the inducability of pENKAT12 in cultured rat astrocytes.

Dose response curves for the effect of dopaminergic agonists on the inducability of pENKAT12 in cultured rat astrocytes was generated using the above methods, as shown in FIGS. 8–11. Dopamine and apomorphine have both D1 and D2 receptor agonist activities [Kebabian and Calne, Nature 277:93–96 (1979)] and they both induce episomal pENKAT12 plasmid expression (under control of the human ppEnk promoter) about 19 fold when present at $10^{-5}$ Molar (FIGS. 8 and 9). SKF38393-R(+) (FIG. 10) is a D1 agonist and LY17155 (FIG. 11) is a D2 agonist.

Additionally, the responsiveness of the transfected cultures to serotonergic (5HT) agonists was assessed. Cultured primary astrocytes have been reported to have functional 5HT receptors [Hertz et al., Can J Physiol Pharmacol 57:223–226 (1979); Hosli and Hosli, Neurosci Lett. 65:177–182 (1986); Hansson, Progr in Neurobiol 30:369–397 (1988); Whitaker-Azmitia et al., Brain Res 528:155–158 (1990)] that can be induced to increase c-AMP levels in these glial cells [Hertz et al. (1979); Hosli and Hosli, J Physiol 82:191–195 (1987); Hansson et al., Neurochem Res 9:679–689 (1984); Whitaker-Azmitia, in Glial Cell Receptors, pp. 107–120, ed. Kimelberg, Raven Press, New York (1988)]. Astrocytes were treated with either of three serotonergic agonists, serotonin, 5-methoxytryptamine and buspirone, at the same concentration as the dopaminergic agonists.

Serotonergic agonist treatments showed no significant changes in transfected CAT expression. In these studies, dopamine (10 $\mu$M) treatments of transfected astrocyte cultures were performed in parallel as positive controls.

Figure 12:
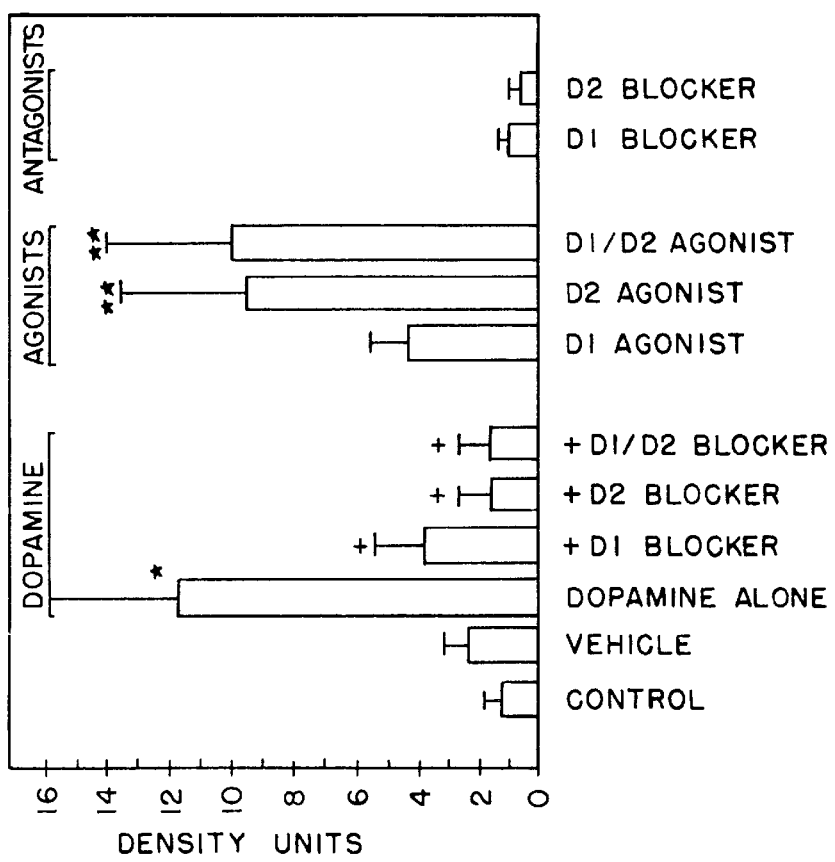
FIG. 12 illustrates that dopaminergic receptor subtypes interact to regulate transfected primary rat astrocytes.

FIG. 12 illustrates that the dopaminergic receptor subtypes interact to regulate transfected primary rat astrocytes. Dopamine alone induced the ppEnk gene and its effects are blocked by appropriate agents. Groups of 6 to 9 dishes were analyzed and data reported as X+/−SEM. Comparisons were made by ANOVA followed by Neuman-Keuls test: * $p<0.005$ vs all other groups; ** $p<0.02$ vs all other groups except D1 agonist, D2 agonist, and D1+D2 agonist groups; +$p<0.001$ from dopamine alone as are the vehicles and both blockers alone. All drugs were used at 10 $\mu$M for 16 hours. D1 Agonist is SKF38393-R(+); D1 Blocker is SCH39166; D2 Agonist is LY17155; and D2 Blocker is S(−)-Sulpiride.

Regulation of the Endogenous ppENK Gene: Promoter Comparison

Figure 13:
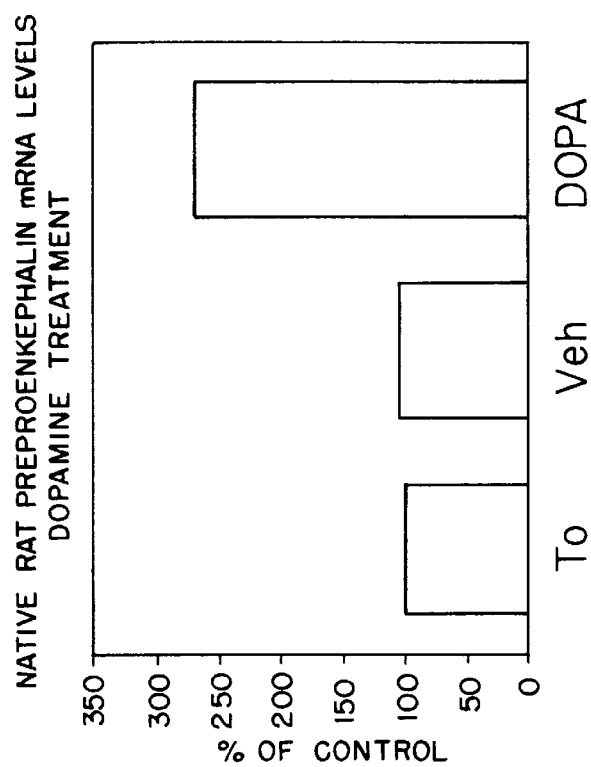
FIG. 13 illustrates that dopamine alone induces the endogenous rat ppEnk gene.

To determine whether the signal transduction pathway involved with the induction of the transfected human ppEnk promoter is relevant to the regulation of the endogenous rat ppEnk gene, northern blot analysis was performed in parallel experiments. The northern data showed that the endogenous rat ppEnk promoter was only marginally induced 2.7 fold (compared to the transfected human exogenous ppEnk promoter) by dopamine (10 $\mu$M) (FIG. 13, $p=0.05$) over the untreated control. This indicates the predominant effect of drug treatment is on the transfected gene.

This highlights a difference between the transfected human ppEnk promoter versus the endogenous rat ppEnk promoter in the same cell background after similar treatments.

These results demonstrate that the human ppEnk promoter transfected into "normal" primary striatal astrocytes can be induced with dopaminergic agonists.

Based on these results, one concludes that L-DOPA, MAO inhibitors, or cholinergic pathway modifiers could be used to induce an engineered ppEnk promoter driven gene of interest (e.g. growth hormones or tyrosine hydroxylase gene) and to control local synthesis of the transfected gene product by dopaminergic pathways. Benefits like this are not currently available from other inducible promoters like the metallothionein [Hamer and Walling, J Mol Appl Genet 1:273–288 (1982)] or the Mouse Mammary Tumor Virus (MMTV) [Yamamoto, in Molecular Developmental Biology: Expressing Foreign Genes, pp. 131–148, ed. Bogorad and Adelman, Alan Liss, New York (1985)] promoters, as the former promoter is induced by heavy metals and the latter by high dose glucocorticoid hormones. The induction of both of these latter promoters in animals would involve toxic treatments or hormonal side effects and hence may not be useful in man. No other inducible promoters have been reported as functional in cells transplanted into the CNS.

In Vivo Regulation of the Human ppEnk Promoter by Dopaminergic Pathways

To determine the extent of dopaminergic influence on basal levels of ppEnk promoter driven CAT activity, animals were unilaterally lesioned with 6-OHD injections into the Substantia Nigra. After establishing abnormal rotational behavior in these rats (Ungerstadt model of Parkinson's Disease), transiently transfected astrocytes (16–18 hours following transfection) were transplanted (500,000 cells/site) into the lesioned and contralateral striatum. Animals were treated with the combined dopaminergic agonist Apomorphine (0.3 mg/kg, ip, QID X4 doses), for 24 hours after transplantation and then sacrificed. The excised transplant-containing tissue blocks were assayed for CAT activity. ppEnk driven CAT activity was significantly ($p<0.05$) lower in all lesioned striata compared to the equivalent unlesioned contralateral brain region, and the ratio of expression between unlesioned and lesioned straita and was further reduced by apomorphine treatment ($p<0.05$). These data confirm the role of basal levels of dopaminergic input in maintaining high levels of expression of the transfected gene in the inervated striatum (see FIG. 2). The apomorphine experiments indicate a pharmacologically induced down regulation of the ppEnk promoter, in vivo, thereby demonstrating control of an inserted gene in transplanted primary cells.

Poison Pill—Herpesvirus Thymidine Kinase

Principle advantages of astrocytes over other cell vehicles are their migratory capacity after transplantation, their regional specificity, and an ability to divide in culture (in vitro). As a result of these properties, and as a safeguard against the possibility of the transplanted cells growing out of hand during in vivo therapy, the invention provides a "poison pill" strategy which will render only transplanted cells susceptible to a pharmacologic agent. Cells modified (for example, using the above methods) to contain the herpes simplex thymidine kinase (HS-TK) gene become sensitive to treatment with the FDA-approved antiviral drugs gancyclovir and acyclovir [Moolten, Cancer Res 46:5276 (1986); Borrelli et al., Proc Natl Acad Sci USA 85:7572 (1988); Moolten and Wells, J Natl Cancer Inst 82:297 (1990); Ezzeddine et al., Neu Biol 3:608 (1991)]. Alternate methods for destroying unwanted transplanted cells would include genetically modifying astrocytes to express the bacterial enzyme cytosine deaminase which converts the generally nontoxic FDA-approved compound 5-fluorocytosine into the toxic product 5-fluorouracil, that will kill the genetically modified cells only [Mullen et al., Proc Natl Acad Sci USA 89:33 (1992)]. This can be most readily accomplished using the methodology of the subject invention by creating a plasmid vector containing a constitutive promoter (e.g. thymidine kinase or RSV as done with the CAT gene) driving a HS-TK reporter/product on the same sequence as the astrocyte-specific promoter GFAP driving a neomycin (G418) selection gene.

The G418 gene allows selective pressure in vitro and the TK poison pill gene allows selective destruction with drugs in vivo. Neither of these approaches will alter the effects of the preceding sections where genetically modified astrocytes express other biologically active compounds. A simpler version of an astrocyte-specific selective pressure plasmid is illustrated in FIG. 7 (pGF8 neo).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A non-virally genetically modified non-tumorous astrocyte comprising:

DNA consisting of a first DNA encoding a selectable marker and a second DNA encoding a biologically active molecule;

wherein expression of the DNA encoding the selectable marker is regulated by the promoter for glial fibrillary acidic protein or by the RSV promoter:

and wherein expression of the DNA encoding the biologically active molecule is regulated by a regulatory element for controlling expression of said DNA encoding the biologically active molecule, said regulatory element including a regulatable promoter which controls expression in said astrocyte, and wherein said first and second DNA, said promoter, and said regulatory element are stably incorporated into the genomic DNA of said astrocyte.

2. The genetically modified astrocyte of claim 1 wherein said selectable marker is a protein conferring neomycin resistance.

3. The genetically modified astrocyte of claim 1 wherein said selectable marker is a protein conferring methotrexate resistance.

4. The genetically modified astrocyte of claim 1 wherein expression of said DNA encoding said biologically active molecule results in the production of a protein.

5. The genetically modified astrocyte of claim 1 wherein said biologically active molecule is a growth factor.

6. The genetically modified astrocyte of claim 1 wherein said biologically active molecule is a cytokine.

7. The genetically modified astrocyte of claim 1 wherein said biologically active molecule is tyrosine hydroxylase.

8. The genetically modified astrocyte of claim 1 wherein said regulatable promoter is an inducible promoter.

9. The genetically modified astrocyte of claim 8 wherein said inducible promoter is a human preproenkephalin promoter.

10. An astrocyte cell line resulting from the genetically modified astrocyte of claim 1.

* * * * *